US012668560B2

(12) United States Patent (10) Patent No.: US 12,668,560 B2

Wiederhold et al. (45) Date of Patent: Jun. 30, 2026

(54) METHOD FOR THE PREPARATION OF 1,2-PROPANEDIOL AND DIPROPYLENE GLYCOL

(71) Applicant: Evonik Operations GmbH, Essen (DE)

(72) Inventors: Holger Wiederhold, Darmstadt (DE); David Bolz, Frankfurt (DE)

(73) Assignee: Evonik Operations GmbH, Essen (DE)

( * ) Notice: Subject to any disclaimer, the term of this patent is extended or adjusted under 35 U.S.C. 154(b) by 546 days.

(21) Appl. No.: 18/249,906

(22) PCT Filed: Oct. 7, 2021

(86) PCT No.: PCT/EP2021/077642

§ 371 (c)(1),
(2) Date: Apr. 20, 2023

(87) PCT Pub. No.: WO2022/084047

PCT Pub. Date: Apr. 28, 2022

(65) Prior Publication Data

US 2023/0382833 A1 Nov. 30, 2023

(30) Foreign Application Priority Data

Oct. 21, 2020 (EP) .................................... 20203081

(51) Int. Cl.
|  |  |
|---|---|
| *C07C 29/48* | (2006.01) |
| *C07C 29/74* | (2006.01) |
| *C07C 41/05* | (2006.01) |

(52) U.S. Cl.
CPC .............. *C07C 29/48* (2013.01); *C07C 29/74* (2013.01); *C07C 41/05* (2013.01)

(58) Field of Classification Search
CPC ......... C07C 29/48; C07C 29/74; C07C 41/05; C07C 31/205; C07C 43/04; B01J 27/188; B01J 31/0237; B01J 31/0239
See application file for complete search history.

(56) References Cited

U.S. PATENT DOCUMENTS 10,214,471 B2 2/2019 Wiederhold et al.
2018/0354878 A1* 12/2018 Wiederhold .......... C07C 29/106

FOREIGN PATENT DOCUMENTS

| CN | 109553593 | 4/2019 |
|---|---|---|
| TW | 201731805 A | 9/2017 |
| WO | 2017/089075 | 6/2017 |

OTHER PUBLICATIONS

International Search report issued Jan. 4, 2022, in PCT/EP2021/077642, 5 pages.
Li et al., "Removing propylene glycol from propylene oxide by direct oxidation of hydrogen peroxide, comprises e.g. mixing a catalyst quaternary ammonium phosphotungstate quaternary ammonium salt with hydrogen peroxide and organic solvent", WPI / 2017 Clarivate Analytics, vol. 2019, No. 43, Apr. 2, 2019, 3 pages.
Written Opinion issued Jan. 4, 2022, in PCT/EP2021/077642, 7 pages.
U.S. Appl. No. 18/249,984, filed Apr. 21, 2023, Wiederhold et al.
U.S. Appl. No. 18/249,724, filed Apr. 19, 2023, Wiederhold et al.
U.S. Appl. No. 18/249,980, filed Apr. 21, 2023, Wiederhold et al.
U.S. Appl. No. 18/249,584, filed Apr. 19, 2023, Wiederhold et al.
U.S. Appl. No. 18/249,695, filed Apr. 19, 2023, Wiederhold et al.
U.S. Appl. No. 18/249,729, filed Apr. 19, 2023, Bolz et al.
U.S. Appl. No. 18/249,908, filed Apr. 20, 2023, Wiederhold et al.
U.S. Appl. No. 18/249,982, filed Apr. 21, 2023, Wiederhold et al.
U.S. Appl. No. 18/249,660, filed Apr. 19, 2023, Wiederhold et al.
U.S. Appl. No. 18/249,825, filed Apr. 20, 2023, Wiederhold et al.
U.S. Pat. No. 10,214,471, Feb. 26, 2019, 2018/0354878, Wiederhold et al.

(Continued)

*Primary Examiner* — Deborah D Carr
(74) *Attorney, Agent, or Firm* — Grüneberg Global IP, PLLC

(57) ABSTRACT

A method for preparing 1,2-propanediol and dipropylene glycol involves continuously reacting propene with hydrogen peroxide in the presence of a catalyst mixture, containing a phase transfer catalyst and a heteropolytungstate, in a liquid reaction mixture containing an aqueous phase with a maximum apparent pH of 6 and an organic phase, to obtain 1,2-propanediol and dipropylene glycol. The method then involves separating the reaction mixture into an aqueous phase ($P_a$) containing 1,2-propanediol and dipropylene glycol and an organic phase ($P_o$); recycling at least part of the separated organic phase ($P_o$) to the reaction; and recovering 1,2-propanediol and dipropylene glycol from the separated aqueous phase ($P_a$). The reaction heat generated is at least partially removed, and the ratio of 1,2 propanediol to dipropylene glycol is controlled by adjusting the weight ratio of hydrogen peroxide to water fed to the reaction.

18 Claims, No Drawings

(56)　　　　　　References Cited

OTHER PUBLICATIONS

Martin et al., "Glycols, Propylene Glycols", The Down Chemical Company, Kirk-Othmer Encyclopedia of Chemical Technology, 10 pages, Downloaded from, https://onlinelibrary.wiley.com/doi/10.1002/0471238961.1618151613011820.a01 by Cochrane Germany, Wiley online library on Nov. 9, 2023.

* cited by examiner

METHOD FOR THE PREPARATION OF 1,2-PROPANEDIOL AND DIPROPYLENE GLYCOL

CROSS-REFERENCE TO RELATED APPLICATIONS

This application is the National Stage entry under § 371 of International Application No. PCT/EP2021/077642, filed on Oct. 7, 2021, and which claims the benefit of priority to European Application No. 20203081.3, filed on Oct. 21, 2020. The content of each of these applications is hereby incorporated by reference in its entirety.

BACKGROUND OF THE INVENTION

Field of the Invention

The present invention relates to a method for the preparation of 1,2-propanediol and dipropylene glycol by reacting propene with hydrogen peroxide wherein the ratio of 1,2-propanediol to dipropylene glycol can be controlled.

Description of Related Art

In a well-established process used in the industry, 1,2-propanediol is prepared by reacting propene oxide with water. Propene oxide can be made on an industrial basis using the HPPO process comprising the reaction of propene with hydrogen peroxide in the presence of a titanium zeolite catalyst and an organic solvent. Propene oxide is isolated and purified prior to a second step of reacting it with water to make 1,2-propanediol. As valuable side product small amounts of dipropylene glycol are obtained. The second step of hydrolyzing propene oxide to 1,2-propanediol is generally run adiabatically and it is difficult to increase the amounts of dipropylene glycol, because adiabatic hydrolysis requires a minimum amount of water to take up the heat of reaction.

WO 2017/089075 discloses a method for producing 1,2-propanediol from propene and hydrogen peroxide comprising: a) reacting propene with hydrogen peroxide in the presence of a catalyst mixture comprising a phase transfer catalyst and a heteropolytungstate, wherein the reaction is carried out in a liquid mixture comprising an aqueous phase with a maximum pH of 6 and an organic phase, b) dividing the two-phase mixture from step a) into an aqueous phase and an organic phase containing propylene oxide, c) returning the propylene oxide contained in the separated organic phase into the reaction from step a) and d) separating 1,2-propanediol from the aqueous phase separated in step b). Furthermore, this document teaches to reduce the amounts of dipropylene glycol and tripropylene glycol by subjecting the aqueous phase separated in step b) to a nanofiltration step wherein a retentate enriched in heteropolytungstate is obtained and recycled to the reaction step a). Thereby, sufficient water is recycled to step a) to maintain a concentration of 1,2-propanediol in the aqueous phase in the range of 10 to 30% by weight.

Both 1,2-propanediol and dipropylene glycol are valuable products, but the demand for these products in the market is fluctuating. Thus, there is a desire in the industry to have a method for the preparation of 1,2-propanediol and dipropylene glycol where the ratio of 1,2-propanediol and dipropylene glycol produced can be easily controlled and changed to accommodate market needs.

SUMMARY OF THE INVENTION

The inventor of the present invention has now found that the ratio of 1,2-propanediol to dipropylene glycol can be adjusted in the two phase oxidation process of WO 2017/089075 by adjusting the weight ratio of hydrogen peroxide to water fed to the reaction step, which allows to obtain a higher proportion of dipropylene glycol than possible for adiabatic hydrolysis of propene oxide.

Subject of the invention is therefore a method for the preparation of 1,2-propanediol and dipropylene glycol comprising:

a) continuously reacting propene with hydrogen peroxide in the presence of a catalyst mixture comprising a phase transfer catalyst and a heteropolytungstate in a liquid reaction mixture comprising an aqueous phase with a maximum apparent pH of 6 and an organic phase to obtain 1,2-propanediol and dipropylene glycol;

b) separating the reaction mixture into an aqueous phase ($P_a$) comprising 1,2-propanediol and dipropylene glycol and an organic phase ($P_o$);

c) recycling at least a part of the separated organic phase ($P_o$) to the reaction step a); and d) recovering 1,2-propanediol and dipropylene glycol from the separated aqueous phase ($P_a$);

wherein the reaction heat generated in step a) is at least partially removed and the ratio of 1,2 propanediol to dipropylene glycol is controlled by adjusting the weight ratio of hydrogen peroxide to water fed to step a), wherein the weight ratio of hydrogen peroxide to water is varied within the range of from 0.05 to 1.5.

DETAILED DESCRIPTION OF THE INVENTION

In the method of the present invention, propene is reacted in a step a) with hydrogen peroxide in the presence of a catalyst mixture comprising a phase transfer catalyst and a heteropolytungstate. This reaction is carried out in a liquid reaction mixture which comprises an aqueous phase with a maximum apparent pH of 6 and an organic phase.

Propene can be used in pure form or in a mixture with propane, wherein the proportion of propane may be up to 20 mol %. The proportion of propane in the propene used is preferably less than 5 mol %. Propene is preferably employed in a molar excess to hydrogen peroxide, preferably in a molar ratio of propene to hydrogen peroxide of from 1.1:1 to 10:1.

Hydrogen peroxide is preferably used in the form of an aqueous solution, preferably with a hydrogen peroxide content of 10 to 80% by weight, particularly preferably 30 to 70% by weight. Any commercially available grade of aqueous hydrogen peroxide solutions can be used. A crude hydrogen peroxide product obtained in the extraction stage of the anthraquinone process for producing hydrogen peroxide may also be used.

The catalyst mixture used in step a) comprises a heteropolytungstate. The heteroatom is preferably phosphorus or arsenic and is particularly preferably phosphorus, i.e. the heteropolytungstate is particularly preferably a polytungstophosphate. Heteropolytungstates are well known to a person skilled in the art. Preferred polytungstophosphates have a molar ratio of phosphorus to tungsten in the range of from 1:2 to 1:12. The polytungstophosphate is preferably generated in situ by combining phosphoric acid and sodium tungstate, which can be carried out in the liquid reaction mixture itself or prior to adding the polytungstophosphate to the liquid reaction mixture. Phosphoric acid and sodium tungstate are preferably employed at a molar ratio of phosphorus to tungsten in the range of from 1:2 to 10:1, preferably from 4:1 to 8:1. The heteropolytungstate reacts with hydrogen peroxide in the liquid reaction mixture to form peroxotungstates and peroxotungstophosphates, for example $PO_4[WO(O_2)_2]_4^{3-}$ and $HPO_4[WO(O_2)_2]_2^{2-}$ as well as partially protonated forms thereof, which are presumably the catalytically active species for oxidizing propene.

The catalyst mixture used in step a) also comprises a phase transfer catalyst. The phase transfer catalyst comprises a cation or a compound which forms a cation in the aqueous phase, whereby the cation can form a salt with a peroxotungstate or heteropolyperoxotungstate, which salt is soluble in the organic phase of the liquid reaction mixture. The phase transfer catalyst preferably comprises a singly-charged cation or a compound which forms a singly-charged cation in the aqueous phase. Suitable as phase transfer catalyst are tertiary amines, tertiary and quaternary ammonium salts, and quaternary phosphonium salts. Suitable counterions for tertiary and quaternary ammonium salts are the anions chloride, bromide, nitrate, sulphate, hydrogen phosphate, dihydrogen phosphate, methyl sulfonate, methyl sulphate and ethyl sulphate. The phase transfer catalyst is preferably used in an amount which results in a molar ratio in the liquid mixture of phase transfer catalyst to tungsten in the range of from 0.2:1 to 3:1 and particularly preferably of from 0.4:1 to 1:1, where the molar ratio refers to the cations or compounds forming cations in the employed phase transfer catalyst and to the employed amount of tungsten.

In a preferred embodiment, the phase transfer catalyst is a tertiary amine or a tertiary or a quaternary ammonium salt which comprises in total at least 12 carbon atoms, preferably from 12 to carbon atoms. Preferred are tetraalkylammonium salts. Suitable tertiary amines are for example dodecyldimethylamine, hexadecyldimethylamine, octadecyldimethylamine, tributylamine and trioctylamine. Suitable tertiary ammonium salts are the protonation products of these teriary amines. Suitable quaternary ammonium salts are for example dodecyltrimethylammonium salts, hexadecyltrimethylammonium salts, octadecyltrimethylammonium salts, methyltributylammonium salts and methyltrioctylammonium salts. More preferably, the phase transfer catalyst comprises a tertiary or quaternary ammonium ion having the structure $R^1R^2R^3NR^{4+}$, wherein $R^1$, $R^2$ and $R^3$ are the same or different and are each selected from alkyl groups having from 8 to 10 carbon atoms and $R^4$ is hydrogen or methyl. Most preferably, the phase transfer catalyst comprises methyltri(octyl/decyl)ammonium methylsulfate (CAS No. 2387913-24-6).

In another preferred embodiment, the phase transfer catalyst comprises at least one salt having a tertiary or quaternary ammonium ion of the structure $R^1R^2R^3R^4N^+$, where $R^1$ is a $Y—O(C=O)R^5$ group with Y being $CH_2CH_2$, $CH(CH_3)$ $CH_2$ or $CH_2CH(CH_3)$ and $R^5$ being an alkyl group or alkenyl group having 11 to 21 carbon atoms, $R^2$ is hydrogen or an alkyl group having 1 to 4 carbon atoms, and $R^3$ and $R^4$ are each independently $R^1$, an alkyl group having 1 to 4 carbon atoms or $Y—OH$. Preferred are quaternary ammonium salts with methylsulphate as the counterion, where $R^2$ is a methyl group and $R^5$ is a linear alkyl group or alkenyl group. Particularly preferred are the salts $(CH_3)_3N^+CH_2CH_2O(C=O)R^5$ $CH_3OSO_3^-$, $(CH_3)_2N^+(CH_2CH_2OH)(CH_2CH_2O$ $(C=O)R^5)$ $CH_3OSO_3^-$, $(CH_3)_2N^+(CH_2CH_2O(C=O)$ $R^5)_2$ $CH_3OSO_3^-$, $CH_3N^+(CH_2CH_2OH)_2(CH_2CH_2O$ $(C=O)R^5)$ $CH_3OSO_3^-$, $CH_3N^+(CH_2CH_2OH)$ $(CH_2CH_2O(C=O)R^5)_2$ $CH_3OSO_3^-$, $CH_3N^+$ $(CH_2CH_2O(C=O)R^5)_3$ $CH_3OSO_3^-$, $(CH_3)_3N^+CH_2CH$ $(CH_3)O(C=O)R^5$ $CH_3OSO_3^-$, $(CH_3)_2N^+(CH_2CH$ $(CH_3)OH)(CH_2CH(CH_3)O(C=O)R^5)$ $CH_3OSO_3^-$ and $(CH_3)_2N^+(CH_2CH(CH_3)O(C=O)R^5)_2CH_3OSO_3^-$, in which $R^5$ is in each case a linear alkyl group or alkenyl group having 11 to 21 carbon atoms. Most preferred is the salt $(CH_3)_2N^+(CH_2CH(CH_3)O(C=O)R^5)_2$ $CH_3OSO_3^-$ in which $R^5$ is an alkyl group or alkenyl group having 11 to 17 carbon atoms. The phase transfer catalysts of this embodiment may be prepared by esterifying ethanolamine, isopropanolamine, diethanolamine, diisopropanolamine, triethanolamine or triisopropanolamine with a fatty acid and subsequent quaternization with dimethyl sulphate. These phase transfer catalysts have the advantage that they are readily biodegradable, unlike tetraalkylammonium salts, and can be introduced into a biological treatment plant without further pretreatment. The salts with methylsulphate as anion are also less corrosive than tetraalkylammonium halides.

The reaction of step a) is carried out in a liquid reaction mixture which comprises two liquid phases, an aqueous phase with a maximum apparent pH of 6 and an organic phase. The term "apparent pH" here refers to a value determined by measurement with a glass electrode employing a commercial pH meter calibrated with aqueous buffer solutions of known pH for measuring dilute aqueous solutions. This apparent pH differs from the notional pH, i.e. the negative logarithm of the hydrogen ion activity, by a constant value because the normal potential of the glass electrode in the aqueous phase of the reaction mixture, which comprises hydrogen peroxide and glycols, is different than the normal potential in pure water. The apparent pH of the aqueous phase is preferably maintained in the range from 1.0 to 3.5, particularly preferably in the range from 2.0 to 3.0. The apparent pH can be maintained in this range by addition of acid, preferably sulphuric acid or phosphoric acid, or by addition of base, preferably aqueous sodium hydroxide solution. Adjusting the apparent pH in the preferred range provides high selectivity for 1,2-propanediol and prevents enriching propene oxide in the aqueous phase, which simplifies the subsequent separation of propylene glycols from the aqueous phase.

In the reaction of step a), the weight ratio of hydrogen peroxide to water fed to step a) is preferably adjusted while maintaining a molar excess of propene to hydrogen peroxide fed to step a). The weight ratio of hydrogen peroxide to water is varied within the range of from 0.05 to 1.5, preferably from 0.10 to 0.7 and more preferably from 0.15 to 0.45. The molar ratio of propene to hydrogen peroxide fed to step a) is preferably from 1.1:1 to 10:1, more preferably from 1.2:1 to 4:1.

The concentration of hydrogen peroxide in the aqueous phase of step a) is preferably kept within a range of from 0.1 to 5% by weight, preferably from 0.12 to 1.0% by weight.

The reaction is preferably conducted at a temperature in the range of from 50 to 110° C., more preferably 60 to 100° C. and particularly preferably 70 to 90° C. The reaction pressure is preferably higher than the vapor pressure of propene at the reaction temperature to ensure that most of the propene is present in the liquid organic phase of the liquid mixture.

The reaction of step a) can be carried out with or without addition of an organic solvent. The reaction is preferably conducted in the presence of at least one organic solvent having a boiling point of more than 100° C., preferably more than 120° C., which has a solubility in water of less than 250 mg/kg at 20° C. Suitable as solvents are alcohols having one or more hydroxyl groups, ethers, esters, ketones and alkylated aromatic hydrocarbons. Adding a solvent can improve extraction of a salt formed of the heteropolytungstate and the phase transfer catalyst into the organic phase. Preferably the amount of organic solvent is selected to provide a proportion of organic solvent in the organic phase during the reaction in the range of from 10 to 90% by weight.

In a preferred embodiment, the organic solvent comprises an epoxidized fatty acid methyl ester. The epoxidized fatty acid methyl ester can be formed in situ in the reaction mixture of step a) by employing a fatty acid methyl ester with unsaturated fatty acid groups which reacts with hydrogen peroxide to the epoxidized fatty acid methyl ester. Particularly preferred are epoxidized fatty acid methyl esters which comprise fatty acid groups originating from vegetable oils, in particular soybean oil. The epoxidized fatty acid methyl esters have the advantage that they have low solubility in the aqueous phase.

In another preferred embodiment, the solvent comprises an alkylated aromatic hydrocarbon having 8 to 12 carbon atoms. Suitable alkylated aromatic hydrocarbons are, for example, 1,2-dimethylbenzene (o-xylene), 1,3-dimethylbenzene (m-xylene), 1,4-dimethylbenzene (p-xylene), ethylbenzene, 1,2,3-trimethylbenzene, 1,2,4-trimethylbenzene, 1,3, 5-trimethylbenzene (mesitylene), 1-ethyl-2-methylbenzene, 1-ethyl-3-methylbenzene and 1-ethyl-4-methylbenzene and n-propylbenzene. Preferably, hydrocarbon mixtures comprising more than 50% by weight, particularly preferably more than 80% by weight, of alkylated aromatic hydrocarbons having 8 to 12 carbon atoms are used as solvent. The use of these solvents enables extracting most of the peroxotungstates into the organic phase of the reaction mixture and recycling them, which allows for operating the process without a need for recovering heteropolytungstate from the aqueous phase of the reaction mixture of step a). The phase transfer catalyst, the molar ratio of phase transfer catalyst to heteropolytungstate, the molar ratio of heteroatom of the heteropolytungstate to tungsten, the molar ratio of propene to hydrogen peroxide and the amount of solvent are then preferably selected to transfer as much as possible of the tungsten present in the liquid reaction mixture into the organic phase.

The phase transfer catalyst, the heteropolytungstate and the optionally used solvent can be added in step a) of the method of the present invention separately or in the form of mixtures containing two or all three of these components. Preferably, a solvent is used in step a) and the phase transfer catalyst and the heteropolytungstate are added dissolved in an organic phase comprising the solvent.

The reaction of step a) may be carried out in batch or continuously, with a continuous reaction being preferred. The concentration of hydrogen peroxide in the aqueous phase is preferably maintained in the range of 0.1 to 5% by weight, particularly preferably 0.5 to 3% by weight. The concentration of hydrogen peroxide can be adjusted in this range by appropriate selection of the reaction temperature, the molar ratio of propene to hydrogen peroxide and the residence time of the liquid mixture in the reactor in which the reaction takes place. The residence time of the reaction mixture is preferably adjusted to maintain a hydrogen peroxide conversion in the range of from 80 to 99%.

During the reaction, the liquid mixture is preferably mixed in order to generate a large phase interface between the aqueous phase and the organic phase. For this purpose, the reaction is preferably carried out continuously in a loop reactor which has fixed internals and the liquid mixture is passed through the loop reactor at a flow rate which generates a turbulent flow at the internals. Baffles, static mixing elements, structured packings or random packings can be used as internals for this purpose. In combination to these internals or as an alternative, heat exchangers, such as plate heat exchangers or tube bundle heat exchangers, may be used, in which turbulent flow is generated, for example between the plates of a plate heat exchanger or in the tubes of a tube bundle heat exchanger.

In step a) of the method of the present invention, the reaction heat generated by the oxidation of propene is at least partially removed. Preferably, all or a part of the generated reaction heat is removed by cooling the reaction mixture in a heat exchanger. More preferably, the reaction is carried out continuously in a loop reactor which comprises a heat exchanger within the reactor loop for cooling the reaction mixture.

In step b) of the method of the present invention, the liquid reaction mixture provided by step a) is separated into an aqueous phase ($P_a$) comprising 1,2-propanediol and dipropylene glycol and an organic phase ($P_o$). The separation of the two-phase reaction mixture provided by step a) is preferably carried out in a settler vessel. The two-phase reaction mixture is preferably passed through a coalescer element comprising a structured packing or a random packing with a surface wetted by the dispersed phase of the two-phase mixture in order to achieve a more complete separation.

The aqueous phase ($P_a$) typically comprises water, unreacted hydrogen peroxide and the reaction products 1,2-propanediol and dipropylene glycol. The aqueous phase typically also contains tripropylene glycol as well as reaction byproducts, such as 1-hydroperoxy-2-propanol and 2-hydroperoxy-1-propanol formed by reaction of propene oxide with hydrogen peroxide, and hydroxyacetone formed by further oxidation of 1,2-propanediol. The aqueous phase typically may also comprise phosphoric acid and sodium salts of phosphoric acid if a polytungstophosphate generated in situ by combining phosphoric acid and sodium tungstate is used in step a). The organic phase ($P_o$) comprises unreacted propene and propene oxide that is formed as intermediate when propene is reacted with hydrogen peroxide and has not been hydrolyzed to 1,2-propanediol. The organic phase ($P_o$) typically also comprises one or more salts formed of the heteropolytungstate and the cation of the phase transfer catalyst. The organic phase ($P_o$) will also comprise propane, if the propene starting material contains propane, and organic solvent, if an organic solvent having a low solubility in water is used as described further above.

In step c) of the method of the present invention, at least a part of the separated organic phase ($P_o$) is recycled to the reaction step a). Thereby, propene oxide present in the organic phase ($P_o$) is recycled to step a) in order to achieve a complete conversion of propene to 1,2-propanediol, dipropylene glycol and tripropylene glycol. Preferably, the heteropolytungstate present in the organic phase ($P_o$) is recycled into step a), and it is particularly preferred to recycle substantially all of the catalyst mixture that is present in the organic phase into step a).

The organic phase ($P_o$) separated from the liquid reaction mixture provided by step a) may be recycled to step a) without further treatment. If the propene fed to step a) contains propane, it is preferred to separate a stream of unreacted propene from the organic phase in step c) before the organic phase is recycled to step a), with the separated stream of unreacted propene containing as much propane as the impure propene fed to step a). This way, an accumulation of propane in the organic phase of the reaction mixture of step a) can be avoided for a continuous reaction. The separated stream of unreacted propene may be passed to a C3 splitter for separating propene and propane and the recovered propene may be recycled to step a).

The aqueous phase ($P_a$) obtained in step b) is preferably further processed without recycling any part of it directly or indirectly to step a).

In a preferred embodiment, the aqueous phase ($P_a$) separated in step b) is subjected to a hydrogenation treatment before it is passed to step d). The hydrogenation is preferably carried out using a supported hydrogenation catalyst comprising one or more metals from the group of Ru, Rh, Pd, Pt, Ag, Ir, Fe, Cu, Ni and Co on a support, wherein activated carbon, $SiO_2$, $TiO_2$, $ZrO_2$, $Al_2O_3$ and aluminium silicates are preferred as support materials. Preference is given to hydrogenation catalysts comprising ruthenium as active metal. The catalytic hydrogenation is preferably carried out at a partial hydrogen pressure of 500,000 Pa to 5,000,000 Pa (5 to 50 bar), preferably 500,000 Pa to 3,500,000 Pa (5 to 35 bar), more preferred 700,000 Pa to 3,000,000 Pa (7 to 30 bar), even more preferred 800,000 Pa to 2,500,000 Pa (8 to 25 bar), and a temperature of 80° C. to 140° C., preferably 90° C. to 120° C. The hydrogenation catalyst may be used as a suspension or as a fixed bed, a trickle bed hydrogenation with a fixed bed catalyst being preferred. The hydrogenation can prevent problems caused by decomposition of hydrogen peroxide, which has not reacted in step a), in step d) of recovering 1,2-propanediol and dipropylene glycol. The hydrogenation also converts the by-products 1 hydroperoxy-2 propanol, 2 hydroperoxy-1 propanol and hydroxyacetone formed in step a) to 1,2-propanediol and thereby improves the yield of 1,2-propanediol.

In step d) of the method of the present invention, 1,2-propanediol and dipropylene glycol are recovered from the optionally hydrogenated aqueous phase of step b). 1,2-Propanediol and dipropylene glycol are preferably recovered by a sequence of distillation steps. Preferably, a sequence of distillation steps as described in Ullmann's Encyclopedia of Industrial Chemistry, online edition, entry "Propanediols", page 4, DOI 10.1002/14356007.a22_163.pub2 is used where an overhead product comprising water is separated from a bottoms product comprising 1,2-propanediol and dipropylene glycol in a series two to four heat integrated distillation steps, followed by successive vacuum distillation steps which provide 1,2-propanediol and dipropylene glycol as overhead products and a bottoms product containing higher boiling organic compounds and salts. From this bottoms product, tripropylene glycol may be recovered as an overhead product in a further vacuum distillation step.

The present invention will now be explained in more detail with reference to examples.

EXAMPLES

Preparation of Initial Epoxidation Catalyst Solution

A mixture of 100 g 70% by weight hydrogen peroxide, 155 g demineralized water, 160 g % by weight phosphoric acid and 100 g sodium tungstate dihydrate was stirred for 2 h at room temperature. Then, a solution of 150 g of methyltri(octyl/decyl)ammonium methylsulfate (CAS No. 2387913-24-6) in 1020 g Hydrosol A 200 ND (a mixture of C10 alkyl benzenes) was added and the mixture was stirred for another 2 h at room temperature. The aqueous and organic phases were then separated to provide 1230 g of organic phase as initial epoxidation catalyst solution.

Reaction of Propene with Hydrogen Peroxide

The reaction of propene with hydrogen peroxide was carried out at a temperature of 80° C. and a pressure of 3,000,000 Pa (30 bar) in a loop reactor with a loop volume of 0.45 l, a circulation pump and a heat exchanger for adjusting the reaction temperature, which was operated at a circulation rate of 130 kg h⁻¹. The reactor was equipped with a catalyst feed reservoir, an organic phase collection vessel equipped with a stirrer, and feed pumps for feeding liquid propene, liquid propane, an aqueous hydrogen peroxide solution and liquid from the catalyst feed reservoir. The initial epoxidation catalyst solution was charged to the catalyst feed reservoir and a mixture of 100 g 70% by weight hydrogen peroxide, 155 g demineralized water, 160 g 85% by weight phosphoric acid and 20 g sodium tungstate dihydrate was charged to the organic phase collection vessel. The loop initially contained reaction mixture from a previous experiment. Circulation was started and maintained at 130 kg h⁻¹ and the circulating mixture was heated to 80° C. Then 80 g h⁻¹ of propene, 50 g h⁻¹ of propane, an aqueous hydrogen peroxide solution containing 0.1% by weight phosphoric acid, and 320 g h⁻¹ of organic catalyst solution from the catalyst feed reservoir were introduced into the loop reactor, cooling the circulating mixture to maintain a reaction temperature of 80° C. The concentration and feed rate of the hydrogen peroxide solution was varied in the three examples to the values given in table 1. A two-phase oxidation reaction mixture was removed from the loop reactor in an amount corresponding to the amounts added and 18 g h⁻¹ of a 9% by weight aqueous disodium sulfate solution was added to this mixture at the reactor outlet to speed up phase separation. The organic phase and the aqueous phase of the resulting mixture were separated, and the organic phase was passed to the organic phase collection vessel after depressurizing and cooling to 25° C. When 500 g of the organic phase had accumulated in the organic phase collection vessel, the content of the vessel was thoroughly mixed by stirring for 5 min, phases were separated by settling and the organic phase was passed to the catalyst feed reservoir with the aqueous phase remaining in the organic phase collection vessel. After about 11 h of operation, the feeding of reactants and the circulation in the loop reactor were stopped and 0.33 g of sodium tungstate dihydrate were charged to the organic phase collection vessel to compensate for losses. The next day, circulation in the loop reactor was restarted, dosing of reactants was resumed after the reaction temperature had been established in the loop reactor and the reaction was continued for another 11 h. The aqueous phase separated from the oxidation reaction mixture was analyzed for hydrogen peroxide by redox titration and for organic products by capillary GC (25 m CP-WAX-52 CB column from Agilent, He carrier gas, temperature program starting at 50° C. with ramps of 20 K/min to 90° C., 10 K/min to 220° C. and 5 K/min to 235° C., FID detector) and ¹H-NMR. Table 2 shows the analysis data obtained after a steady state operation was reached.

9

TABLE 1

Concentration and feed rate of the hydrogen peroxide solution and weight ratio of hydrogen peroxide to water fed to the reactor

| Example | $H_2O_2$ concentration in % by weight | $H_2O_2$ feed rate in g/h | Weight ratio $H_2O_2$ to water |
|---|---|---|---|
| 1 | 30.0 | 116 | 0.429 |
| 2 | 25.0 | 139 | 0.334 |
| 3 | 15.0 | 210 | 0.177 |

TABLE 2

Composition of the aqueous phase (all values in % by weight, except for MPG/DPG ratio)

| Example | $H_2O_2$ | MPG[1] | DPG[2] | TPG[3] | Hydroxy acetone | Acetic acid | MPG/DPG ratio |
|---|---|---|---|---|---|---|---|
| 1 | 0.4 | 27.1 | 6.2 | 1.0 | 0.6 | 0.2 | 4.37 |
| 2 | 0.3 | 24.2 | 5.0 | 1.0 | 0.6 | 0.2 | 4.84 |
| 3 | 0.2 | 18.3 | 2.3 | 0.2 | 0.3 | 0.1 | 7.96 |

[1]1,2-propanediol
[2]dipropylene glycol
[3]tripropylene glycol

From the date in table 2 it is apparent that the ratio of 1,2-propanediol to dipropylene glycol increases with decreasing the weight ratio of hydrogen peroxide to water fed to the reactor. The formation of acetic acid increases only slightly with increasing concentration of hydrogen peroxide, resulting in a slightly reduced selectivity. Thus, it is evident that the weight ratio of 1,2-propanediol to dipropylene glycol can be controlled by adjusting the weight ratio of hydrogen peroxide to water fed to the reactor without compromising the selectivity of the reaction.

The invention claimed is:

1. A method for the preparation of 1,2-propanediol and dipropylene glycol, the method comprising:
   a) continuously reacting propene with hydrogen peroxide in the presence of a catalyst mixture, comprising a phase transfer catalyst and a heteropolytungstate, in a liquid reaction mixture comprising an aqueous phase with a maximum apparent pH of 6 and an organic phase, to obtain 1,2-propanediol and dipropylene glycol;
   b) separating the liquid reaction mixture into an aqueous phase ($P_a$) comprising 1,2-propanediol and dipropylene glycol, and an organic phase ($P_o$);
   c) recycling at least a part of the separated organic phase ($P_o$) to a); and
   d) recovering the 1,2-propanediol and the dipropylene glycol from the separated aqueous phase ($P_a$);
   wherein reaction heat generated in a) is at least partially removed,
   adjusting a ratio of the 1,2-propanediol to the dipropylene glycol by adjusting a weight ratio of the hydrogen peroxide to water fed to a),
   wherein the weight ratio of the hydrogen peroxide to water is varied within a range of from 0.05 to 1.5; and
   wherein the ratio of 1,2-propanediol to dipropylene glycol is reduced by increasing the weight ratio of hydrogen peroxide to water fed to a) or the ratio of 1,2-propanediol to dipropylene glycol is increased by reducing the weight ratio of hydrogen peroxide to water fed to step a).

2. The method of claim 1, wherein the weight ratio of the hydrogen peroxide to water fed to a) is adjusted while maintaining a molar excess of the propene to the hydrogen peroxide fed to a).

3. The method of claim 2, wherein a molar ratio of the propene to the hydrogen peroxide fed to a) is from 1.1:1 to 10:1.

4. The method of claim 1, wherein the weight ratio of the hydrogen peroxide to water is varied within the range from 0.10 to 0.7.

5. The method of claim 1, wherein a concentration of the hydrogen peroxide in the aqueous phase of a) is from 0.1 to 5% by weight.

6. The method of claim 1, wherein a residence time of the liquid reaction mixture in a) is adjusted to maintain a hydrogen peroxide conversion in the range of from 80 to 99%.

7. The method of claim 1, wherein a) is conducted in a loop reactor, and the reaction heat generated in a) is at least partially removed by circulating the liquid reaction mixture through a heat exchanger.

8. The method of claim 1, wherein the aqueous phase ($P_a$) obtained in b) is further processed without recycling any part directly or indirectly to a).

9. The method of claim 1, wherein in d), the aqueous phase ($P_a$) is subjected to catalytic hydrogenation.

10. The method of claim 1, wherein a) is conducted in the presence of phosphoric acid, and wherein the heteropolytungstate is a polytungstophosphate.

11. The method of claim 1, wherein the organic phase in a) comprises an organic solvent having a boiling point of more than 100° C. at atmospheric pressure and a solubility in water at 20° C. of less than 250 mg/kg.

12. The method of claim 1, wherein the phase transfer catalyst comprises at least one selected from the group consisting of a tertiary amine, a tertiary ammonium salt, and a quaternary ammonium salt, and
   wherein the tertiary amine, the tertiary ammonium salt, and the quaternary ammonium salt each comprises in total at least 12 carbon atoms.

13. The method of claim 12, wherein the phase transfer catalyst comprises a tertiary or quaternary ammonium ion having the structure $R^1R^2R^3NR^{4+}$,
   wherein $R^1$, $R^2$, and $R^3$ are the same or different and are each an alkyl group having from 8 to 10 carbon atoms, and
   $R^4$ is hydrogen or methyl.

14. The method of claim 1, wherein b), c), and d) are carried out continuously.

15. The method of claim 3, wherein the molar ratio of the propene to the hydrogen peroxide fed to a) is from 1.2:1 to 4:1.

16. The method of claim 4, wherein the weight ratio of the hydrogen peroxide to water is varied within the range from 0.15 to 0.45.

17. The method of claim 5, wherein the concentration of the hydrogen peroxide in the aqueous phase of a) is from 0.12 to 1.0% by weight.

18. The method of claim 11, wherein the organic solvent is an alkylated aromatic hydrocarbon having 8 to 12 carbon atoms.

* * * * *